Figure 1:
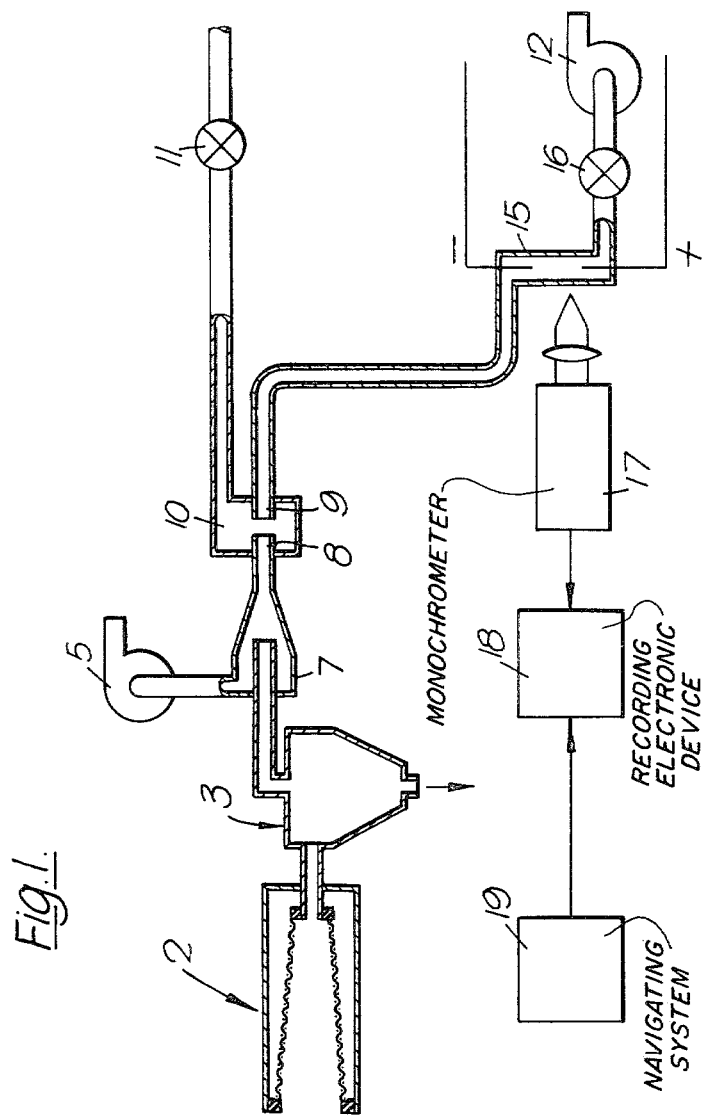

United States Patent [19]

Macourt

[11] 4,338,029
[45] Jul. 6, 1982

[54] MINERAL EXPLORATION

[76] Inventor: Denis J. C. Macourt, 73 Dickson Ave., Artarmon, New South Wales, Australia

[21] Appl. No.: 964,121

[22] Filed: Nov. 28, 1978

[51] Int. Cl.³ .................. G01N 21/62; G01N 31/12; G01N 33/24
[52] U.S. Cl. .............................. 356/311; 23/230 EP; 73/23; 356/36; 356/316
[58] Field of Search ............ 356/36, 311, 313–318; 23/230 EP; 73/28, 23

[56] References Cited

U.S. PATENT DOCUMENTS

| | | | |
|---|---|---|---|
| 3,759,617 | 9/1973 | Barringer | 356/36 |
| 3,868,222 | 2/1975 | Barringer | 23/230 EP |
| 3,970,428 | 7/1976 | Barringer | 23/230 EP |
| 3,998,734 | 12/1976 | Barringer | 73/28 X |
| 4,023,398 | 5/1977 | French et al. | 73/23 |
| 4,056,969 | 11/1977 | Barringer | 23/230 EP X |
| 4,137,750 | 2/1979 | French et al. | 73/23 |

*Primary Examiner*—F. L. Evans

[57] ABSTRACT

A method and apparatus for mineral, in particular hydrocarbon exploration in which determination is made of whether substances indicative of a deposit are present in the atmosphere in the form of charges, molecules or clumps of molecules. Intaken air is purged of particles and only small naturally charged molecules or clumps are transferred to, for instance, an inert gas for spectroscopic examination.

21 Claims, 2 Drawing Figures

MINERAL EXPLORATION

DESCRIPTION

This invention relates to mineral exploration, in particular, though not exclusively, exploration to locate hydrocarbon, that is oil and natural gas, deposits.

For some time now efforts have been made to locate mineral deposits, in particular hydrocarbon deposits of oil and natural gas, by traversing an area of the sea or land which is to be explored in a vehicle such as an aeroplane, and collecting particles which are in suspension in the atmosphere. The idea is that particles above, or down wind of, a deposit will display abnormally high concentrations, which are referred to as anomalies, of elements in or associated with the deposit. Such an anomaly arises, it is thought, by the elements being present upon the particles as adsorbed coatings, and in the context "coating" includes cases where individual or a number of atoms or molecules adhere to the particle surface, as well as cases of a complete or substantial covering of the particle. The coatings are taken to be representative of the geochemical and other characteristics of the area, and the coatings, particularly of larger particles, which are expected to have travelled less far from the source before losing or changing their coatings, can be, and in common practice are, analysed. There are various batch methods of making such analysis, although these are rather slow and unreliable and have to be performed some time after the particles are collected. An alternative and continuous method of analysis which can be performed for instance in an aeroplane is spectroscopy, such as emission, absorption or mass spectroscopy. Thus, it has been proposed to introduce collected particles directly into a plasma and examine the spectrum of light emitted. In order to reduce the problem of interference between individual weak spectral lines attributable to the coatings and strong lines attributable to the particles, and the problem that there may be a variable thermal load in the plasma due to variations in the number of particles collected and their size, and as the larger particles tend to interfere with the field of view, it has further been proposed to volatilize the coatings in a first plasma and carry the volatilized coatings, but not the particles, into a second plasma in which the spectrum of light from the coating is observed. The secondary plasma has a more constant thermal load than the first, it allows a better field of view and the emitted light can more readily be viewed by a spectroscope and subjected to normal spectroscopic analysis.

In connection with exploration for hydrocarbon deposits, it has recently been suggested that, using this technique of examining particle coatings, one should look not only for hydrocarbons themselves, or anomalous spectral lines attributable thereto, but also, or alternatively, for anomalies of the gas radon and/or a halogen, notably iodine. A first reason for this is that the usual hydrocarbon spectral bands can be rather easily confused with the lines of unrelated compounds. A second reason is that halogens (particularly iodine) and uranium are always present anomalously in hydrocarbon deposits. Uranium decays to radium, which decays to inter alia, radon gas (atomic number 88, atomic weight 222). Thus, simultaneous anomalies or radon and/or iodine and hydrocarbon suggest a hydrocarbon deposit much more positively than a mere hydrocarbon anomaly which might arise for other reasons. To date, however, such proposals have been restricted to the consideration of particle coatings and at present all efforts in this field are directed to the analysis of particle coatings.

It is now believed that it may not be necessary, and indeed is undesirable, to collect airborne particles and investigate their coatings. On the contrary, it is now considered that there is evidence for supposing that molecules representative of a deposit are present in the atmosphere above the deposit, unattached to particles, probably in clusters or "clumps" of up to 30 molecules or more. These are, it is now believed, charged, but only retain the charge for a short time because of collisions with ions of opposite charge or adsorption onto dust particles. It is believed these molecules or clumps are dispersed upwards in the atmosphere by rising currents of air and predominantly by the force of the earth's electric field. While it can not be said that they are not present as coatings on atmospheric particles such as dust or salt particles, it is believed that they exist as such, unattached. Moreover, it is believed that at least in the case or hydrocarbon deposits, the molecules or clumps are negatively charged. It is not known why this should be so, but it seems possible that as the uranium in the deposit decays $\alpha$-particles ionise molecules which, in the course of their movement form the clusters or clumps which are negatively charged. These pass to and through the earth's surface as negative ions.

In its first and broadest aspect, therefore, the present invention provides a method of mineral exploration by traversing an area to be explored and determining whether substances indicative of a mineral deposit are present to an anomalous extent in the atmosphere in the form of charged molecules or charged clumps of molecules.

The invention more particularly provides a method of exploration by traversing an area to be explored and determining whether substances indicative of a hydrocarbon deposit are present to an anomalous extent in the atmosphere in the form of charged molecules or charged clumps of molecules.

In the case of exploration for hydrocarbon deposits, the substances to be detected will be hydrocarbons and preferably also halogens, in particular iodine, and/or uranium or more exactly, a product of uranium decay, in particular the gas radon. Exploration will preferably be conducted in an aircraft and detection will preferably be conducted by spectroscopy, preferably emission spectroscopy and, desirably, in the aircraft so that continuous monitoring can be performed.

In performing this method, samples of air may be collected in the vehicle, for instance through a special intake at the front of an aircraft, and it is preferable to collect and/or pass the air through one or more devices which concentrate the molecules and preferably also reject extraneous matter such as dust and insects. To these ends, air can be collected through an electrostatic focussing tube or an aerodyne tube which is insulated and arranged to give a focussing effect and it is preferably then passed through a centrifuge such as a cyclone in order to concentrate and discharge extraneous matter. For instance, particles greater than 0.5 to 1 $\mu$m in size can be rejected. While it is preferable to employ at least one of the aerodyne tube and centrifuge, there may be circumstances in which neither is strictly required. The air can be stored for later analysis or, more preferably, particularly as radon decays quite rapidly (it has a half life of about 3.7 days) the molecules are immediately subject to analysis preferably by spectroscopic analysis. Arrangements can be made to relate the results of the analysis with the particular geographical position at which the sample concerned was taken, as has been done before in the analysis of particle coatings. However, as it is believed the charges dissipate relatively rapidly, the results obtained will be characteristic of the immediate area of collection, in contrast to known methods based on particle collection which required an estimate of displacement.

In order to perform spectroscopic analysis to detect anomalies in the occurence of such molecules or clumps, it is necessary to transfer the molecules from the air in which they are collected into an inert gas by which they are passed to a zone in which the plasma is formed.

When, according to the former exploration techniques, particle coatings were analyzed by spectroscopy, one method of performing such transfer was to pass the collected air, after cyclonic concentration of the particle content, to a device which provided for the air flow to meet an opposite flow of the inert gas, whereon the air was drawn off to one side and some of the particles continued, due to their momentum, through the "barrier" of the inert gas into a second flow of inert gas in the same direction as the original air flow. By the second flow, the particles are carried to the plasma zone. During their passage the particles can be counted in a particle counter if desired. The inert gas is, for this purpose, fed to a tube which is coaxial with the air tube and in which the inert gas flows on the one hand towards the air tube so as to form the barrier and also in another stream away from the air tube to carry transferred particles to the plasma zone. The various flows were adjusted so that only larger particles, which are expected to be more representative of the locality, for instance those exceeding 30 microns or even 10 or 5 microns in diameter, are carried through the plasma zone, the rest being repelled at the barrier and being drawn off with the air.

It is not possible directly to apply this technique to the transfer of molecules or clumps from air to an inert gas because the molecules will have insufficient momentum to penetrate the barrier, which must be of at least a few centimeters in length in order to ensure that the air does not enter the plasma zone. Moreover, of course, some particles will inevitably remain in the airstream even after centrifuging and these must be repelled at the barrier in order to put the invention into effect.

It is proposed to overcome this difficulty by taking advantage of the fact that the molecules or clumps are charged. Thus, according to a second aspect of the invention it is proposed that the charged molecules be transferred from the air in which they are collected to an inert gas by causing the air and inert gas to meet at a boundary at which there is an interface between the air and the inert gas, and causing the charged molecules to traverse the interface into the inert gas by the application of electrical or magnetic fields.

The air will be withdrawn from the region of the interface. In a preferred method it is arranged for a first stream of inert gas to flow towards the interface and counter to the air flow and for a second stream of inert gas to be further from the interface and to flow away from it, in the same direction as the air flow.

Thus, the first inert gas stream "seals" subsequent parts of the apparatus against ingress of air and particles, and the molecules are caused to traverse the seal in order to be carried by the second stream to a plasma zone.

It is also proposed to provide apparatus in which charged molecules can be transferred from air to an inert gas and comprising a first, air guide, tube through which in use collected air is passed, a second, inert gas, tube through which inert gas can be supplied to meet the air at a boundary at which there is an interface between the air and the inert gas, and electrical or magnetic means for causing the charged molecules in the air to traverse the interface into the inert gas.

Preferably, the tubes are arranged so that the air and a first stream of inert gas flow towards one another at the interface and there is a supply of inert gas to form that first stream and a second stream which flows in the same direction as the air from a position downstream of the interface in the original direction of air flow. Thus, the inert gas can be supplied to the second tube through an inlet spaced from the end of the tube adjacent the air tube, in the two streams, which flow away from one another. In use, the second stream of inert gas carries transferred charged molecules towards a plasma zone where a plasma can be created and spectroscopic analysis performed.

Alternatively the tubes can be side by side with an aperture from one to the other to provide the interface.

The means to transfer the charged molecules across the barrier can take a wide variety of forms, for instance appropriately positioned magnetic coils with stationary or oscillating magnetic fields can be provided or electrodes with means for charging them can be located at suitable positions. One particularly convenient way of causing the transfer is to employ the air flow through the air tube itself to generate a negative electrostatic charge on the tube, and this can be done by including in the tube, which is otherwise of an insulating material, a part which is conductive and which is insulated. If, for instance, this part converges to a sharp edge at the end of the tube, then the frictionally developed charge will tend to concentrate at that edge and the fields created can cause the charged molecules to be concentrated in the centre of the tube and to be projected across the interface into the inert gas, rather than be carried further along by the air flow. It is strongly preferable, indeed it is probably essential for practical purposes, for a part of the inert gas tube remote from the barrier also to be of a conductive material, preferably earthed, for instance to the airframe if an aeroplane is employed.

A result of the invention is that only molecules or clumps which are naturally ionised and, it appears, naturally charged, are in general collected.

In addition to the above mentioned aspects independently, the invention provides a method of mineral exploration involving traversing an area to be explored and determining whether substances indicative of a mineral deposit are anomalously present in the atmosphere in the form of charged molecules or clumps of molecules, the method involving collecting air and transferring the charged molecules from the air to an inert gas for the purpose of spectroscopic analysis by causing the air and inert gas to meet at a boundary at which there is an interface between the air and the inert gas, and causing the charged molecules to traverse the interface into the inert gas by the application of electrical or magnetic fields.

The invention further provides apparatus for use in such a method comprising means to be mounted on a vehicle and to collect air, such means being connected to a first, air guide tube through which in use collected air is passed, a second, inert gas, tube through which inert gas can be supplied to meet the air at a boundary at which there is an interface between the air and the inert gas, and electrical or magnetic means for causing the charged molecules in the air to traverse the interface into the inert gas. Such apparatus may, of course, include means for forming a plasma and performing spectroscopic analysis, and may also include an aerodyne tube to collect the air, and a centrifuge to rid the air of particles and extraneous matter.

Figure 2:
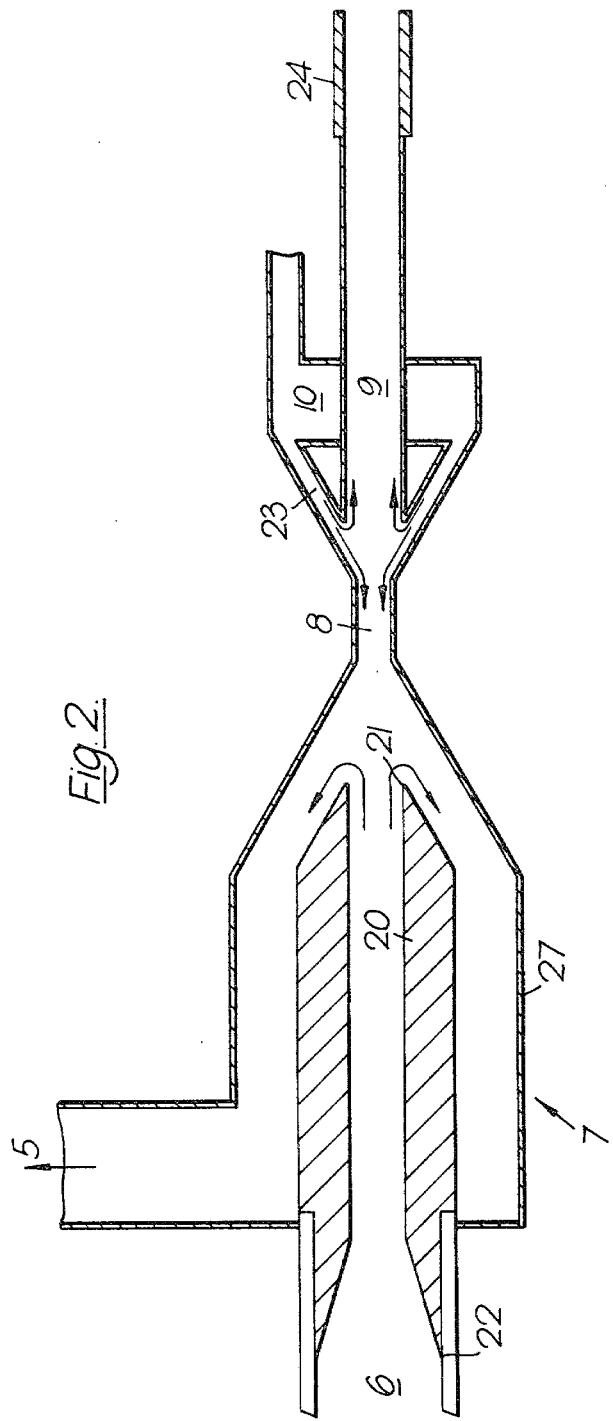

Any aerodyne may be in the form of an inlet which converges in the direction of incoming air flow and is formed of a plurality of baffles. Such arrangements are already known, but according to a preferred feature it is further proposed that the baffles be conductive and be mounted in an insulating manner. If this is done, frictionally generated negative charge on the baffles will tend to concentrate charged molecules centrally of the inlet, particularly when the apparatus includes an earthed member downstream of the baffles.

An alternative inlet arrangement has a conical, insulated wire mesh, converging in to inlet direction and connected, in insulating manner to an intake tube. This mesh will become negatively charged, by air friction, and force small molecule clumps, but not large ones or any particles, towards the centre so that they pass down the tube. Other matter passes through the mesh and is discharged.

In a cyclone or centrifuge, the inside walls will be charged by air friction so as to concentrate the charged molecules in the centre; they are then ejected from the narrow, light fraction end in a cyclone. A cascade of cyclones can be employed.

In order that the invention may be more clearly understood the following description is given by way of example only with reference to the accompanying drawings in which:

FIG. 1 is a schematic side view of apparatus for collecting air and performing spectrometry on molecules and ions entrained therewith;

FIG. 2 is a more detailed sectional view of part of the apparatus FIG. 1.

As shown in FIG. 1, apparatus which may be located in an aircraft includes an air intake 2 which will project out of the aircraft to collect air, and is in the form of an aerodyne tube, or preferably and as shown, of a tube with a conically convergent insulated wire mesh therein, leading to a cyclone 3 for differentially concentrating particulate matter towards the outside for discharge, and a tube 6 by which the air and charged molecules are conducted to a device 7 at which the charged molecules are transferred from the air to an inert gas supplied to an inlet chamber 10 by a tube having a valve 11, and entering from the inlet chamber 10 into tubes 8 and 9. The inert gas flows in the tube 8 towards the air flow and forms a barrier therewith in the tube 8 and the air, which is stopped in its original direction of flow, is exhausted from the device 7 by a fan 5; charged molecules in the air, however, are caused to traverse the barrier of inert gas by electrical or magnetic means and enter the tube 9 in which there is an inert gas flow in the same direction as the original air flow in tube 6 and which conducts the molecules to a plasma zone 15 in which, for instance by means of two electrodes, a plasma (preferably D.C) is generated which can be viewed through a spectrometer or monochrometer 17. The output of this is processed and recorded by an electronic device 18 coupled to a navigating system 19 so that the output of the spectrometer or monochrometer can be correlated with the position of the aircraft over the ground. Of course the plasma need not be an electrode plasma, radio frequency or microwave plasmas can be used instead if desired and indeed mass spectroscopy could be employed. A further pump 12 draws the inert gas through the plasma at a rate controlled by a valve 16, which should give a constant flow.

In order to cause the charged molecules to traverse the barrier from the air flow into the inert gas an electromagnetic arrangement, for instance coils surrounding the molecule path, can be provided. Alternatively an electrostatic arrangement can be employed. FIG. 2, which is a more detailed view of part of the apparatus of FIG. 1, shows one such electrostatic arrangement.

In this arrangement, the air inlet tube 6 has a terminal portion 20 which is of a conductive material and is mounted in an insulating manner. This terminal portion 20 is surrounded by a shroud 27 of the device 7 which has an outlet leading to the fan 5 of FIG. 1. Aligned with the portion 20 is the tube 8 which is in turn aligned with the tube 9 and between the tubes 8 and 9 are orifices of inlet conduits 23 for inert gas supplied from the chamber 10. Beyond the inlet orifices is a further conductive part 24 of the tube 9 electrically connected to a shroud 27. However, the portion 20 is the only part of the apparatus illustrated in this Figure which has to be of conductive material. In use, the air flow through the tube 6 and any particles therein meet and are stopped by an opposite flow of inert gas in the tube 8 supplied through the conduits 23. Thus, the air flow should not be so great, or the inert gas flow so low, that particles or air are transferred.

The air is exhausted through the shroud 27 by the fan 5. Downstream of the orifices of conduits 23 the inert gas flow is in the same direction as the original air flow so as to carry charged molecules which traverse the barrier between the air and inert gas to subsequent stages. The air flow over the portion 20 and shroud 27 cause them to be negatively charged by friction and the charges developed on portion 20 migrate to a large extent to the point 21 which is made as sharp as possible. Provided therefore that the charged molecules are carried by the air flow up to the point 21, the charge at that point will cause them to continue in their path despite the reversal in the air flow. The effect is enhanced by the conductive part 24 by reason of which a strong electric field will exist between parts 20 and 24 which the charged molecules will be unable to cross. Thus, the charged molecules traverse the barrier and pass through the counterflow of inert gas into the flow of inert gas in the tube 9. The portion 20 is also, as shown, provided with a second sharp end 22 and while charge will accumulate here also the construction and air flow can readily be made such that the charge here acts to centre the charged molecules in the air flow rather than to prevent their flow through the portion 20.

The FIG. 2 arrangement as described so far is in effect a simple but automatic arrangement for transferring charged molecules from the air flow to the inert gas flow but it can be improved or modified by simply arranging for selected potentials to be applied to the portion 20 and if desired the part 24. The portion 20 could be biased to increase or decrease the rate of charged molecule transfer to the inert gas and in this case it might not be necessary to shape the portion 20 as it is shown in FIG. 2. Similarly, part 24 could be biased as desired to affect the charged molecule flow through the tube 9. It will normally be desirable to prevent airborne particles which are collected at the same time as the charged molecules from being transferred into the inert gas and thence to the plasma. To a large extent this can be arranged by the centrifuge already described which can separate down to 1 μm, but in addition can be affected by adjusting the air and inert gas flows in the tubes 6 and 8 and by appropriate selection of the lengths of tubes 8 and 9. In addition a particle collector could be located in the tube 9 and if desired a particle counter can be included in the tube 9 to assess the effectiveness of the measures taken to keep particles out of the tube. Such a counter can be constructed as an interruption in the tube 9 surrounded by an inert gas containing chamber and in which a light beam can be employed in a known manner with a photoelectric device to count particles crossing the gap. To protect the plasma zone further from the presence of undesired particles, a filtering arrangement can be employed between the tube 9 and the plasma zone, such as a thermostatically controlled oven enclosing a sintered porous filter to collect any particles which are inadvertently transferred into the inert gas and conveyed to that point. The oven is heated to prevent the adsorption of the charged molecules on the filter; it facilitates the transport of the molecules to the plasma and the resultant pre-heating of the gas facilitates the operation and striking of the plasma, but this may not be necessary.

A grid can be provided at the interface between air and inert gas, with biasing means so as to shut off or encourage charged molecule flow in a controlled manner.

It will be appreciated that the practice of this invention is based on the belief that the molecules or clumps are charged. If this is correct, then under fair weather conditions the clumps or molecules will generally travel straight upwards due to the earth's electric field. This belief is reinforced by the fact that it is found that in conditions where the electric field of the earth is disturbed, e.g. at cold fronts, sea mists and thunderstorms, the invention cannot be efficiently practised because the number of such molecules or clumps to be collected is significantly reduced.

I claim:

1. A method of mineral exploration which comprises the steps of: traversing an area to be explored; sampling atmospheric air while conducting such tranverse; separating charged molecules and charged clumps of molecules from such sampled air; determining the extent to which substances indicative of a mineral deposit are present in such charged molecules and charged clumps of molecules and determining whether such substances are present to an anomalous extent indicative of a mineral deposit.

2. A method as claimed in claim 1 in which the charged molecules and charged clumps of molecules are separated from the air by transferring them to an inert gas stream from the air, such transfer being effected by causing the air and inert gas to meet at a boundary at which there is an interface between them through which particulate matter in the air will not pass, and applying an electrical or magnetic field to cause the charged molecules to traverse the interface into the inert gas.

3. A method as claimed in claim 2 wherein the air and a first stream of inert gas are caused to flow towards the interface from opposite directions, the air is withdrawn from the interface, and a second stream of inert gas is flowed away from the interface from a position removed from the interface.

4. A method according to claim 3 wherein the air is fed towards the interface through a tube which terminates adjacent the interface, at least a part of the tube being of insulated conductive material.

5. A method according to claim 1 including the step of correlating the determination with the immediate position in the traverse.

6. A method of exploration which comprises the steps of: traversing an area to be explored; sampling atmospheric air while conducting such traverse, separating charged molecules and charged clumps of molecules from such sampled air; determining the extent to which substances indicative of a hydrocarbon deposit are present in such charged molecules and charged clumps of molecules and determining whether such substances are present to an anomalous extent indicative of a hydrocarbon deposit.

7. A method as claimed in claim 6 wherein the substances in respect of which determination is made are hydrocarbons.

8. A method as claimed in claim 6 wherein the substances in respect to which determination is made are halogens, in particular iodine.

9. A method as claimed in claim 6 wherein the substances in respect of which determination is made are at least one of uranium and products of uranium decay in particular radon.

10. A method as claimed in claim 6 wherein the step of sampling includes the steps of collecting air through an intake of an aircraft in which the traverse is conducted, and concentrating the charged molecules or clumps and rejecting extraneous matter prior to the step of separation of charged molecules and charged clumps of molecules.

11. A method as claimed in claim 10 wherein the step of concentration is conducted using at least one of: an aerodyne tube; an inlet provided with an insulated convergent wire mesh leading to a pipe; and a centrifuge, such as a cyclone; and wherein particulate matter in excess of 1 micron in size is rejected.

12. A method as claimed in claim 6 wherein the step of determination is conducted by spectroscopy, in particular emission spectroscopy.

13. A method of mineral exploration which comprises the steps of: traversing an area to be explored; collecting atmospheric air during such traverse, separating particulate matter from the collected air; transferring charged molecules and charged clumps of molecules from the air to an inert gas, such transfer being effected by causing the air and inert gas to meet at a boundary at which there is an interface between the air and the inert gas, applying an electrical or magnetic field to cause the charged molecules and charged clumps of molecules to traverse the interface into the inert gas, spectroscopically analysing the molecules and clumps so transferred, determining the extent to which samples indicative of a mineral deposit are present in such molecules and clumps and determining whether such substances are present to an anomalous extent indicative of a mineral deposit.

14. A method of exploration which comprises the steps of: traversing an area to be explored; collecting atmospheric air during such traverse, separating particulate matter from the collected air; transferring charged molecules and charged clumps of molecules from the air to an inert gas; such transfer being effected by causing the air and inert gas to meet at a boundary at which there is an interface between the air and inert gas, applying an electrical or magnetic field to cause the charged molecules and clumps of molecules to traverse the interface into the inert gas, spectroscopically analysing the molecules and clumps so transferred, determining the extent to which samples indicative of a hydrocarbon deposit are present in such molecules and clumps, and determining whether such substances are present to an anomalous extent indicative of a hydrocarbon deposit.

15. Apparatus for use in mineral, in particular hydrocarbon, exploration by traversing an area to be explored, such apparatus comprising means defining an intake for sampling air; a centrifuge to concentrate charged molecules and charged clumps of molecules occuring in the sampled air and to reject extraneous matter from the air; means to separate the concentrated charged molecules and charged clumps of molecules from such sampled air; and means for determining the extent to which substances indicative of a mineral deposit are present in such charged molecules and charged clumps of molecules.

16. Apparatus according to claim 15 and further comprising, as the intake, one of: an aerodyne tube having baffles of conductive material mounted in an insulating manner, and a conduit provided internally with an insulated convergent wire mesh leading to a pipe.

17. Apparatus as claimed in claim 15 including a spectrometer with which the determination is performed.

18. Apparatus as claimed in claim 15 including means to transfer charged molecules and charged clumps of molecules from the air to an inert gas, such means including a first, air guide passage through which in use collected air is passed, a second, inert gas passage through which in use an inert gas can be supplied to meet the air at a boundary at which there is an interface between the air and inert gas, and means for applying one of an electrical and magnetic field for causing the charged molecules in the air to traverse the interface into the inert gas.

19. Apparatus as claimed in claim 18 wherein said passages are so arranged that in use the air and a first stream of inert gas flow towards one another at the interface and including means to provide a first supply of inert gas to form that first stream and a second supply of inert gas which flows in the same direction as the air from a position downstream of the interface in the original direction of air flow.

20. Apparatus as claimed in claim 19 wherein said air passage terminates adjacent the interface, at least a part of said passage being of insulated, conductive material.

21. Apparatus for use in mineral, in particular hydrocarbon, exploration by traversing an area to be explored, such apparatus being locatable on a vehicle and comprising in combination an intake for sampling air, means for rejecting extraneous particulate matter from the sampled air and means to transfer charged molecules and clumps of molecules from the sampled air to an inert gas, such transfer means comprising a first, air guide, passage through which in use the air is passed and a second, inert gas, passage through which an inert gas can be supplied to meet the air at a boundary at which there is an interface, and means for applying one of an electrical and magnetic field for causing the charged molecules in the air to traverse the interface into the inert gas, and means for performing spectroscopic analysis.

* * * * *

UNITED STATES PATENT AND TRADEMARK OFFICE
CERTIFICATE OF CORRECTION

PATENT NO. : 4,338,029

DATED : July 6, 1982

INVENTOR(S) : DENIS J. C. MACOURT

It is certified that error appears in the above-identified patent and that said Letters Patent are hereby corrected as shown below:

On the title page, column 1 insert the following:

[30]   Foreign Application priority data

Nov. 29, 1977   Great Britain..............49710/77

Column 2, line 22, "case or" should read --case of--.

Column 7, line 49, "transverse" should read --traverse--.

Column 9, line 18, "occuring" should read --occurring--.

Signed and Sealed this

Eighth   Day of   February 1983

[SEAL]

Attest:

GERALD J. MOSSINGHOFF

Attesting Officer   Commissioner of Patents and Trademarks